(12) United States Patent
Knodel et al.

(10) Patent No.: US 7,918,376 B1
(45) Date of Patent: *Apr. 5, 2011

(54) ARTICULATED SURGICAL INSTRUMENT

(75) Inventors: Bryan D. Knodel, Flagstaff, AZ (US);
Bennie Thompson, Cincinnati, OH
(US); Philipe R. Manoux, San
Francisco, CA (US); Nathan H. White,
Redwood City, CA (US)

(73) Assignee: Cardica, Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/400,760

(22) Filed: Mar. 9, 2009

(51) Int. Cl.
*A61B 17/064* (2006.01)
(52) U.S. Cl. ............... 227/175.1; 227/19; 606/219
(58) Field of Classification Search ........... 439/447, 439/173
See application file for complete search history.

(56) References Cited

U.S. PATENT DOCUMENTS

| | | | |
|---|---|---|---|
| 2,515,366 A | 7/1950 | Zublin | |
| 3,191,455 A | 6/1965 | Fuqua T. et al. | |
| D210,021 S * | 1/1968 | Prifogle et al. | D13/154 |
| 3,497,608 A * | 2/1970 | Hoffer et al. | 174/135 |
| 3,581,551 A | 6/1971 | Wilkinson | |
| 3,583,393 A | 6/1971 | Takahashi | |
| 3,650,453 A * | 3/1972 | Smith, Jr. | 227/138 |
| 3,837,555 A * | 9/1974 | Green | 227/130 |
| 3,899,914 A | 8/1975 | Akiyama | |
| 3,986,765 A * | 10/1976 | Shaffer et al. | 439/314 |
| 4,086,926 A | 5/1978 | Green et al. | |
| 4,127,227 A * | 11/1978 | Green | 227/83 |
| 4,228,895 A | 10/1980 | Larkin | |
| 4,328,839 A | 5/1982 | Lyons et al. | |
| 4,475,679 A | 10/1984 | Fleury, Jr. | |
| 4,600,037 A | 7/1986 | Hatten | |
| 4,633,861 A | 1/1987 | Chow et al. | |
| 4,762,260 A | 8/1988 | Richards et al. | |
| 4,869,414 A | 9/1989 | Green et al. | |
| 4,969,591 A | 11/1990 | Richards et al. | |
| 5,042,707 A * | 8/1991 | Taheri | 606/213 |
| 5,143,475 A | 9/1992 | Chikama | |
| 5,156,315 A | 10/1992 | Green et al. | |
| 5,192,288 A | 3/1993 | Thompson et al. | |
| 5,271,543 A * | 12/1993 | Grant et al. | 227/179.1 |

(Continued)

FOREIGN PATENT DOCUMENTS

EP          1238634          9/1994

(Continued)

OTHER PUBLICATIONS

Gong, Shao W., "Perfectly flexible mechanism and integrated mechanism system design", *Mechanism and Machine Theory 39 (2004)*, (Nov. 2004),1155-1174.

(Continued)

*Primary Examiner* — Rinaldi I. Rada
*Assistant Examiner* — Lindsay Low
(74) *Attorney, Agent, or Firm* — Brian A. Schar (57) ABSTRACT

One example of a surgical instrument may include a handle, an end effector, and a shaft that connects the handle to the end effector, where the shaft includes an articulated region. At least one feeder belt may extend through the lumen of the shaft into the end effector, where at least one feeder belt may include at least one staple frangibly connected thereto.

6 Claims, 6 Drawing Sheets

U.S. PATENT DOCUMENTS

| | | | |
|---|---|---|---|
| 5,340,330 A * | 8/1994 | Dolson et al. | 439/447 |
| 5,381,943 A | 1/1995 | Allen et al. | |
| 5,405,073 A * | 4/1995 | Porter | 227/175.1 |
| 5,413,272 A | 5/1995 | Green et al. | |
| 5,448,989 A | 9/1995 | Heckele | |
| 5,476,206 A | 12/1995 | Green | |
| 5,485,952 A | 1/1996 | Fontayne | |
| 5,580,067 A | 12/1996 | Hamblin et al. | |
| 5,655,698 A | 8/1997 | Yoon | |
| 5,662,260 A | 9/1997 | Yoon | |
| 5,673,840 A * | 10/1997 | Schulze et al. | 227/175.1 |
| 5,692,668 A | 12/1997 | Schulze et al. | |
| 5,704,534 A * | 1/1998 | Huitema et al. | 227/175.1 |
| 5,749,828 A | 5/1998 | Solomon et al. | |
| 5,772,578 A | 6/1998 | Heimberger et al. | |
| 5,807,241 A | 9/1998 | Heimberger | |
| 5,810,855 A | 9/1998 | Rayburn et al. | |
| 5,816,471 A | 10/1998 | Plyley et al. | |
| 5,823,066 A | 10/1998 | Huitema et al. | |
| 5,855,311 A | 1/1999 | Hamblin et al. | |
| 5,857,964 A | 1/1999 | Konstorum et al. | |
| 5,894,979 A | 4/1999 | Powell | |
| 5,918,791 A | 7/1999 | Sorrentino et al. | |
| 5,964,774 A | 10/1999 | McKean et al. | |
| 6,053,922 A | 4/2000 | Krause et al. | |
| 6,306,149 B1 | 10/2001 | Meade | |
| 6,364,828 B1 | 4/2002 | Yeung et al. | |
| 6,391,038 B2 | 5/2002 | Vargas et al. | |
| 6,431,904 B1 * | 8/2002 | Berelsman | 439/447 |
| 6,602,252 B2 | 8/2003 | Mollenauer | |
| 6,656,195 B2 | 12/2003 | Peters et al. | |
| 6,716,232 B1 | 4/2004 | Vidal et al. | |
| 6,755,338 B2 * | 6/2004 | Hahnen et al. | 227/175.1 |
| 6,786,382 B1 | 9/2004 | Hoffman | |
| 6,817,508 B1 | 11/2004 | Racenet | |
| 6,827,601 B1 * | 12/2004 | Haeberle | 439/447 |
| 6,843,403 B2 | 1/2005 | Whitman | |
| 7,025,747 B2 | 4/2006 | Smith | |
| 7,097,089 B2 | 8/2006 | Marczyk | |
| 7,140,527 B2 | 11/2006 | Ehrenfels et al. | |
| 7,168,604 B2 | 1/2007 | Milliman et al. | |
| 7,172,104 B2 | 2/2007 | Scirica et al. | |
| 7,179,267 B2 | 2/2007 | Nolan et al. | |
| 7,207,471 B2 | 4/2007 | Heinrich et al. | |
| 7,213,736 B2 | 5/2007 | Wales et al. | |
| 7,225,963 B2 | 6/2007 | Scirica | |
| 7,225,964 B2 | 6/2007 | Mastri et al. | |
| 7,234,624 B2 | 6/2007 | Gresham et al. | |
| 7,238,195 B2 | 7/2007 | Viola | |
| 7,300,297 B1 * | 11/2007 | Wang | 439/173 |
| 7,316,575 B2 * | 1/2008 | Muschketat | 439/76.1 |
| 7,407,077 B2 * | 8/2008 | Ortiz et al. | 227/176.1 |
| 7,434,716 B2 * | 10/2008 | Viola | 227/176.1 |
| 7,486,994 B2 * | 2/2009 | Zarembo et al. | 607/116 |
| 7,506,790 B2 * | 3/2009 | Shelton, IV | 227/176.1 |
| 7,507,109 B2 * | 3/2009 | Tran | 439/456 |
| 7,575,144 B2 * | 8/2009 | Ortiz et al. | 227/175.1 |
| 7,617,961 B2 * | 11/2009 | Viola | 227/175.1 |
| 7,654,838 B1 * | 2/2010 | Zhuge | 439/173 |
| 7,670,334 B2 | 3/2010 | Hueil et al. | |
| 7,708,182 B2 * | 5/2010 | Viola | 227/178.1 |
| 7,819,298 B2 | 10/2010 | Hall et al. | |
| 2003/0120284 A1 | 6/2003 | Palacios et al. | |
| 2003/0236551 A1 | 12/2003 | Peterson | |
| 2005/0184121 A1 | 8/2005 | Heinrich | |
| 2005/0272978 A1 | 12/2005 | Brunnen et al. | |
| 2006/0011699 A1 | 1/2006 | Olson et al. | |
| 2006/0025811 A1 * | 2/2006 | Shelton, IV | 606/205 |
| 2006/0041273 A1 | 2/2006 | Ortiz et al. | |
| 2006/0047307 A1 * | 3/2006 | Ortiz et al. | 606/219 |
| 2006/0151567 A1 | 7/2006 | Roy | |
| 2007/0027472 A1 | 2/2007 | Hiles et al. | |
| 2007/0034668 A1 | 2/2007 | Holsten et al. | |
| 2007/0073341 A1 | 3/2007 | Smith et al. | |
| 2007/0083234 A1 | 4/2007 | Shelton, IV et al. | |
| 2007/0118163 A1 | 5/2007 | Boudreaux et al. | |
| 2007/0125828 A1 | 6/2007 | Rethy et al. | |
| 2007/0175947 A1 * | 8/2007 | Ortiz et al. | 227/175.1 |
| 2007/0221700 A1 * | 9/2007 | Ortiz et al. | 227/175.1 |
| 2007/0221701 A1 * | 9/2007 | Ortiz et al. | 227/175.1 |
| 2008/0249364 A1 | 10/2008 | Korner | |
| 2008/0257935 A1 * | 10/2008 | Viola | 227/176.1 |
| 2009/0076506 A1 | 3/2009 | Baker | |
| 2009/0090764 A1 * | 4/2009 | Viola | 227/176.1 |
| 2009/0177041 A1 | 7/2009 | Stefanchik et al. | |

FOREIGN PATENT DOCUMENTS

| | | |
|---|---|---|
| JP | 2005160933 | 6/2005 |
| RU | 2080833 | 6/1997 |
| WO | WO-81/01953 | 7/1981 |
| WO | WO-85/01427 | 4/1985 |
| WO | WO 2004/103430 | 12/2004 |

OTHER PUBLICATIONS

Lim, Jonas J., et al., "A review of mechanism used in laparascopic surgical instruments", *Mechanism and Machine Theory 38*, (2003),1133-1147.

Lim, Jyue B., "Type Synthesis of a Complex Surgical Device", *Masters Thesis*, (Feb. 21, 2001).

Lim, Jonas J., et al., "Application of Type Synthesis Theory to the Redesign of a Complex Surgical Instrument", *Journal of Biomechanical Engineering (124)*, (Jun. 2004),265-272.

Kolios, Efrossini et al., "Microlaparoscopy", *J. Endourology 18(9)*, (Nov. 2004),811-817.

Steichen, Felicien M., et al., "Mechanical Sutures in Surgery", *Brit. J. Surg. 60(3)*, (Mar. 1973),191-197.

"Cardica Microcutter Implant Delivery Device 510(k)," Cover Sheet, Table 10.1, "Substantial Equivalence Comparison," and Section 12, "Substantial Equivalence Discussion", Oct. 18, 2010.

* cited by examiner

ARTICULATED SURGICAL INSTRUMENT

FIELD OF THE INVENTION

The invention generally relates to an articulated surgical instrument, and more specifically to an instrument that may be used to articulate a surgical stapler or endocutter.

BACKGROUND

Minimally invasive surgery is performed through small incisions in the body, into which trocar ports may or may not be placed. One or more surgical instruments are inserted through each incision in order to perform the surgical procedure. In order to effectuate one of the objectives of minimally invasive surgery, which is the minimization of incisions to the body to reduce healing time and scarring, it is desirable to minimize the number of incisions made in the body. The number of incisions and their placement are determined by the particular surgical procedure to be performed and the configuration of the instruments used to carry out that procedure.

One problem encountering during the performance of a minimally invasive surgical procedure is access to the tissue to be treated. Depending on the specific anatomy of the patient, it may be difficult to reach an area to be treated with a specific surgical instrument. As a result, one or more additional incisions may need to be made in the patient in order to access that tissue. Or, the surgeon may need to obtain a different surgical instrument, adding to the time and expense of the procedure. Additionally, where more incisions may be made or additional instruments may be utilized, it can be difficult and/or time-consuming for the surgeon to find the surgical site again.

BRIEF DESCRIPTION OF THE DRAWINGS

The use of the same reference symbols in different figures indicates similar or identical items.

DETAILED DESCRIPTION

U.S. patent application Ser. No. 11/851,379, filed Sep. 6, 2007; U.S. patent application Ser. No. 11/956,988, filed Dec. 14, 2007; and U.S. patent application Ser. No. 12/263,171, filed Oct. 31, 2008 (the "Endocutter Applications") are hereby incorporated by reference herein in their entirety.

Surgical Instrument

Figure 1:
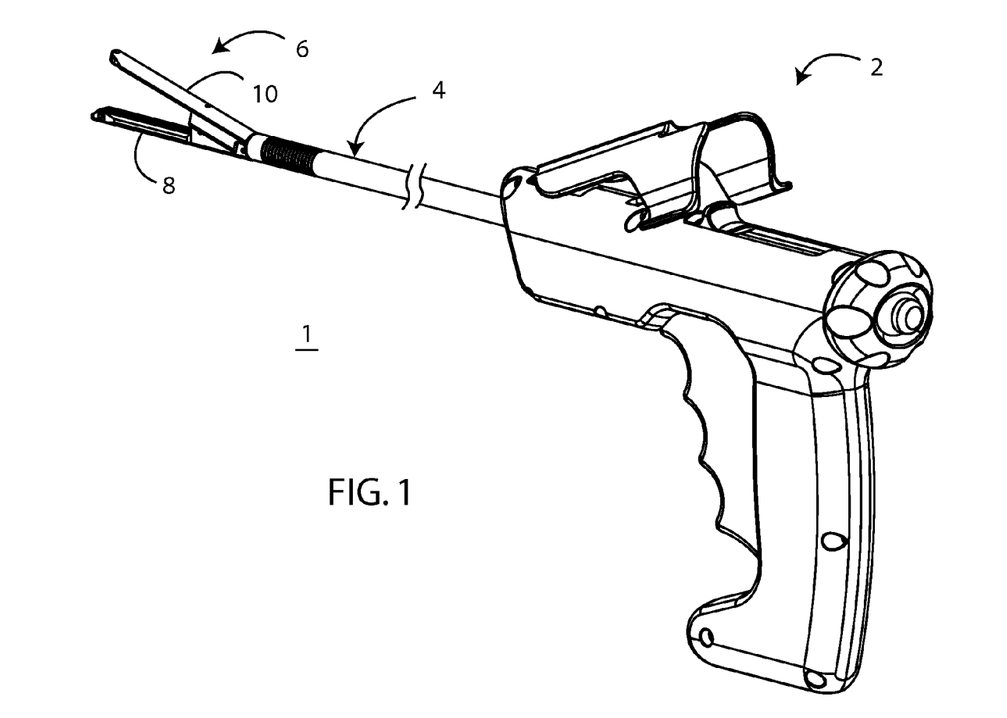
FIG. 1 is a perspective view of a an exemplary surgical instrument.

Referring to FIG. 1, a surgical instrument 1 includes a handle 2 attached to a shaft 4, which in turn is attached to an end effector 6. The surgical instrument 1 may be an endocutter, a linear cutter, a stapler, or any other suitable surgical instrument. The end effector 6 may be one or more separate components that are connected to the shaft 4, or may be fabricated integrally with the distal end of the shaft 4. As discussed in greater detail below, the end effector 6 may be fixed to the shaft 4, or may be separable from the shaft 4 such that a fresh end effector 6 may be attached to the shaft 4 after one or more actuations of the surgical instrument. The end effector 6 and at least the distal end of the shaft 4 may be sized to pass through an incision or through a standard trocar port that may be placed in the patient. Advantageously, the end effector 6 may be sized to pass through a trocar port, having an opening between 5-10 millimeters in diameter. Alternately, the surgical instrument 1 may be used in the course of conventional open surgery, where a trocar port is not used. The end effector 6 may include a staple holder 8 connected to an anvil 10, and may be movable between an open configuration and a closed configuration. In the closed configuration, tissue may be clamped between the staple holder 8 and the anvil 10. Alternately, the end effector 6 may omit the anvil 10. Alternately, the end effector 6 need not include a staple holder 8 or anvil 10, and the end effector 6 may instead be a different surgical instrument, such as but not limited to a bipolar cutter, a biopsy device, a grasper, or a stabilizer.

Figure 2:
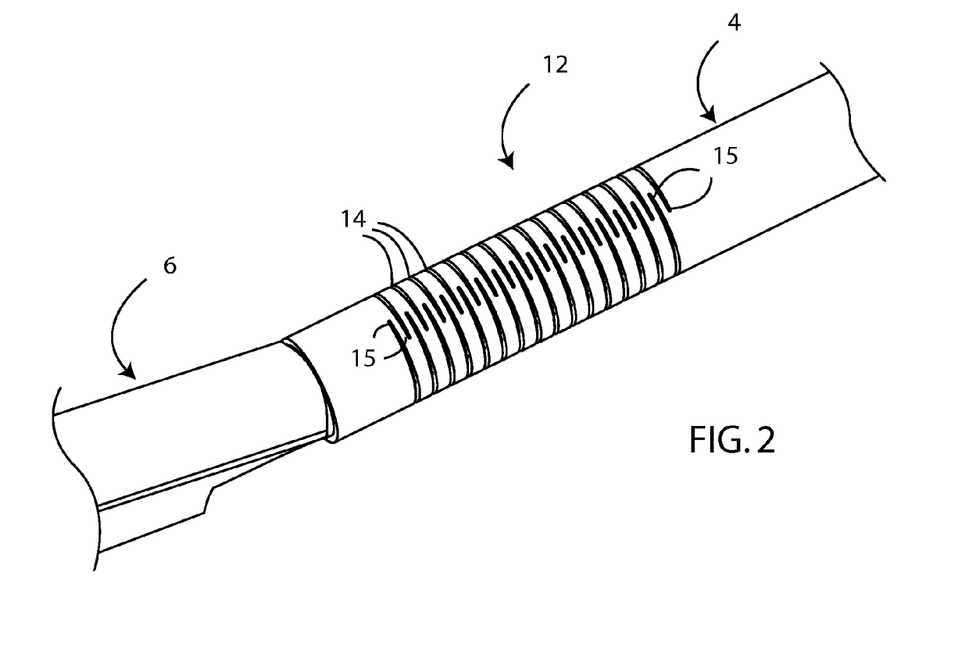
FIG. 2 is a detail perspective view of an exemplary articulated region on a shaft of the surgical instrument of FIG. 1.

The shaft 4 advantageously has a tubular shape with a lumen defined therein. Optionally, the shaft 4 may include a cutaway, trough or other feature (not shown) to allow a guidewire (if any) or other positioning aid that may be used in the surgical procedure to remain in place during actuation of the surgical instrument 1. The shaft 4 may be flexible or rigid, in whole or in part. The shaft 4 may be articulated in at least one location, if desired. Referring to FIG. 2, as one example, the shaft 4 may be generally rigid, with the exception of a flexible articulated region 12 that connects two generally-rigid segments of the shaft 4. A plurality of slots 14 may be located in the shaft 4 in the articulated region 12. The slots 14 may extend completely through the wall of the shaft 4 from the outer surface of the shaft to the lumen in the shaft 4. The slots 14 may be arranged in any suitable manner. As one example, each slot 14 may extend along greater than 180 degrees of circumference of the shaft 4, between two vertices 15. Proceeding proximally along the shaft 4, at least two slots 14 may be generally arranged in an alternating manner. That is, one slot 14 may open generally in one direction away from the longitudinal centerline of the shaft 4, and the slot 14 proximal to that may open generally in the opposite direction away from the longitudinal centerline of the shaft 4. To accomplish this, the vertices 15 of a slot opening (for example) laterally to the left may be located laterally to the right of the vertices of a longitudinally adjacent slot opening laterally to the right. As a result, where at least two slots 14 extend along greater than 180 degrees of circumference of the shaft 4, no line on the surface of the shaft 4 that is parallel to the longitudinal centerline of the shaft 4 can extend completely through the articulating region 12 without encountering a slot 14. Put another way, every line on the surface of the shaft 4 that is parallel to the longitudinal centerline of the shaft 4 crosses at least slot 14. The slots 14 may be oriented and arranged relative to one another to provide for lateral articulation of the shaft 4. That is, the slots 14 may be oriented and arranged such that the portion of the shaft 4 distal to the articulating region 12 is rotatable in a single plane, laterally left and right. Alternately, the slots 14 may be oriented and arranged such that the portion of the shaft 4 distal to the articulating region 12 is rotatable in a single plane in a direction other than laterally left and right. Alternately, the slots 14 may be oriented and arranged such that the portion of the shaft 4 distal to the articulating region 12 is rotatable in more than a single plane.

At least one slot 14 may be angled. That is, extending outward from a vertex 15 of the slot 14, the walls of the slot may be angled relative to one another rather than parallel. Such an angle facilitates bending of the articulated region 12. Advantageously, at least one slot 14 has an angle of substantially two degrees between its walls. However, the angle may be different, or the walls may instead be substantially parallel to one another. The width and angle of each slot 14 may be selected to affect the total amount of travel of the articulating section. Advantageously, the articulating section 12 is bendable such that the portion of the shaft 4 distal to the articulating section 12 is movable through substantially ninety degrees relative to the portion of the shaft 4 proximal to the articulating section, where 45 degrees of such movement is on either side of the longitudinal centerline of the shaft 4. Alternately, the articulating section 12 may be configured to allow a different amount of movement, either greater than or less than ninety degrees. Alternately, the articulating section 12 may be configured to allow movement in more than one plane, in either the same or different amounts in either plane. Alternately, the articulating section 12 may be configured to allow asymmetrical articulation, wherein the distal end of the shaft 4 distal to the articulating section may be movable through a first angle on one side of the longitudinal centerline of the shaft 4 that is greater than a second angle on the other side of the longitudinal centerline of the shaft 4.

Figure 3:
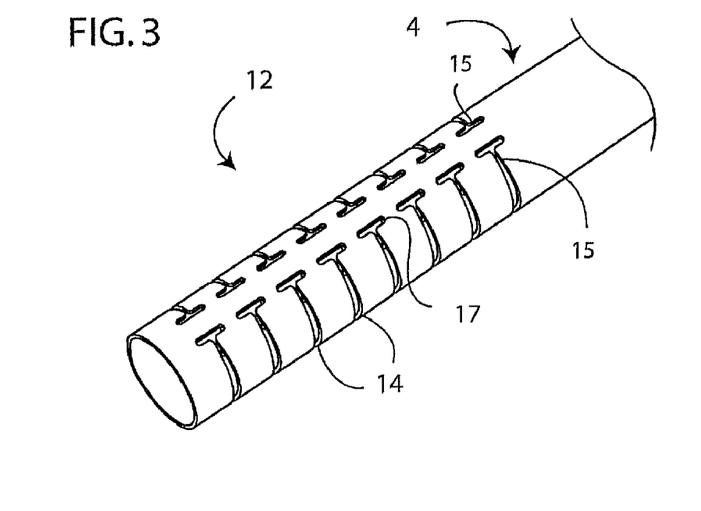
FIG. 3 is a detail perspective view of a second exemplary articulated region on a shaft of the surgical instrument of FIG. 1.

Referring to FIG. 3, another example of an articulating region 12 is shown. The slots 14 may be configured similarly to those described above with regard to FIG. 2. However, at least one of the slots 14 may extend along less than 180 degrees of circumference of the shaft 4. If all of the slots 14 do so, then the slots 14 may be arranged such that a line on the surface of the shaft 4 that is parallel to the longitudinal centerline of the shaft 4 can extend completely through the articulating region 12 without encountering a slot 14. One or more slots 14 may be connected to a longitudinal aperture 17 at a vertex 15 thereof, such that the slot 14 may have a T-shaped appearance if viewed from above. The presence of the longitudinal aperture 17, and its length, provide for greater flexibility of the articulated region 12. The longer the longitudinal aperture 17, the more flexible the articulated region 12.

The handle 2 may be attached to the proximal end of the shaft 4, or any other suitable portion of the shaft 4. The shaft 4 may be fabricated integrally with the handle 2. Alternately, the shaft 4 and the handle 2 may be two separate items that are connected together in any suitable manner. The handle 2 may include any mechanism, mechanisms, structure or structures that are suitably configured to actuate the end effector 6. The handle 2 may also include a source of stored energy for actuating the end effector 6. The source of stored energy may be mechanical (such as a spring), electrical (such as a battery), pneumatic (such as a cylinder of pressurized gas) or any other suitable source of stored energy. The source of stored energy, its regulation, and its use in actuating the end effector 4 may be as described in the U.S. patent application Ser. No. 11/054,265, filed on Feb. 9, 2005, which is herein incorporated by reference in its entirety. The handle 2 may instead, or also, include a connector or connectors suitable for receiving stored energy from an external source, such as a hose connected to a hospital utility source of pressurized gas or of vacuum, or an electrical cord connectable to a power source.

Figure 4:
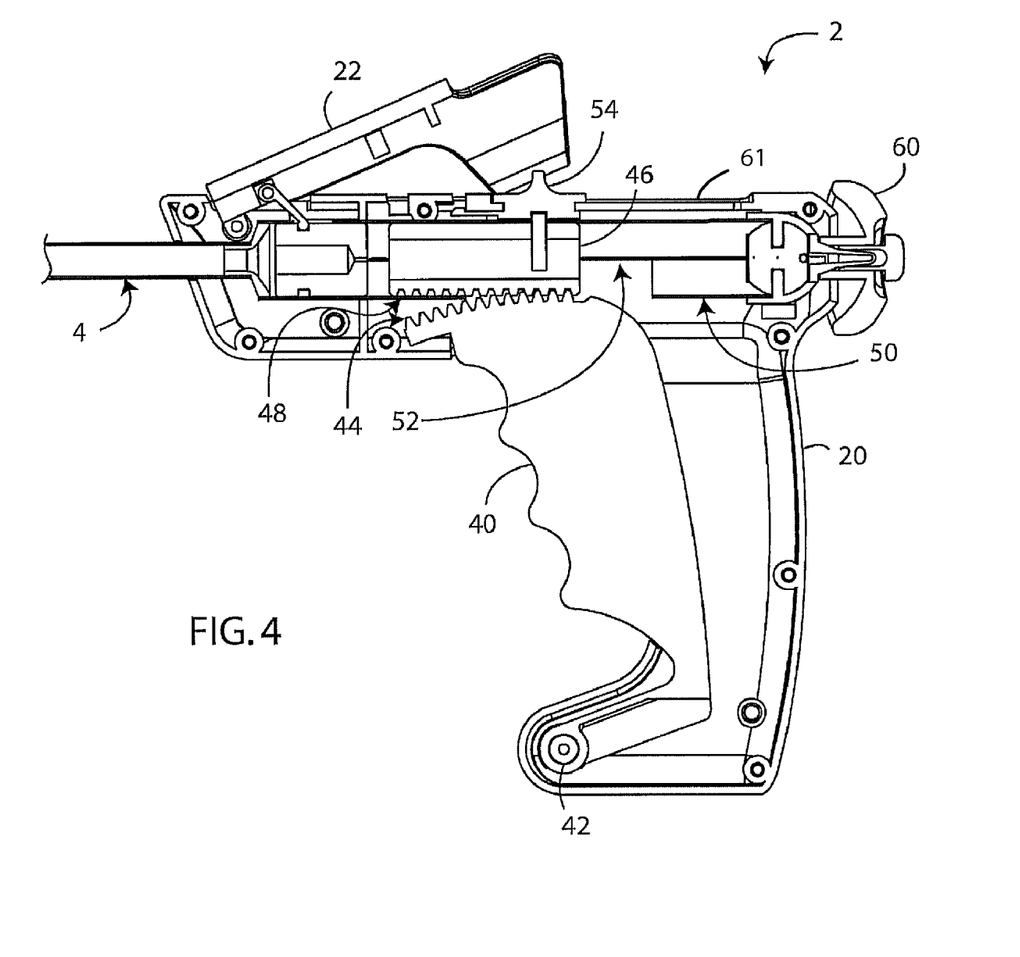
FIG. 4 is a side cutaway view of a handle of the surgical instrument of FIG. 1.
Figure 6:
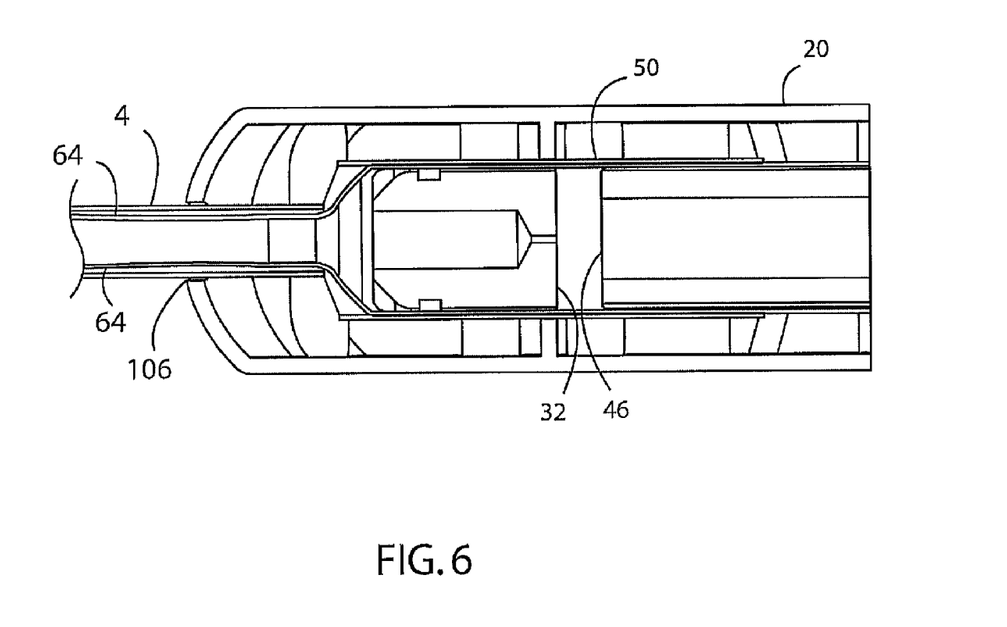
FIG. 6 is a top cross-section view of a handle of the surgical instrument of FIG. 1.
Figure 7:
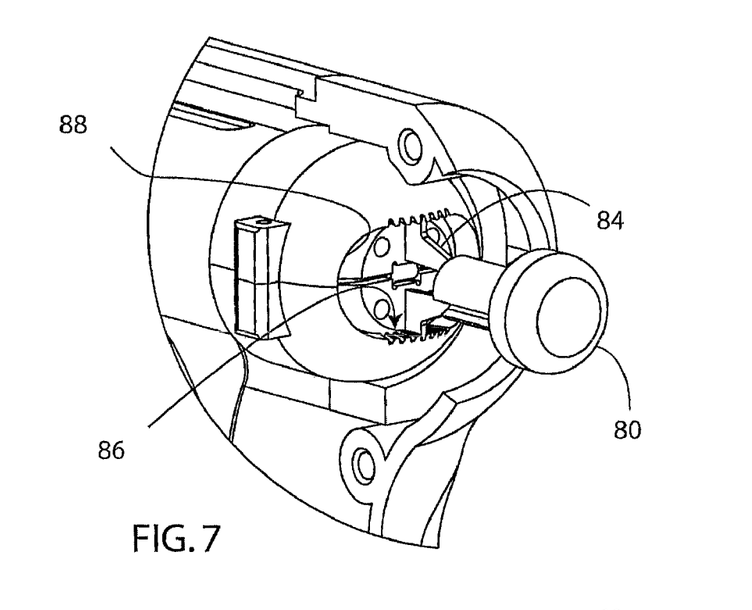
FIG. 7 is a detail cutaway view of a portion of the proximal end of the handle of the surgical instrument of FIG. 1.
Figure 8:
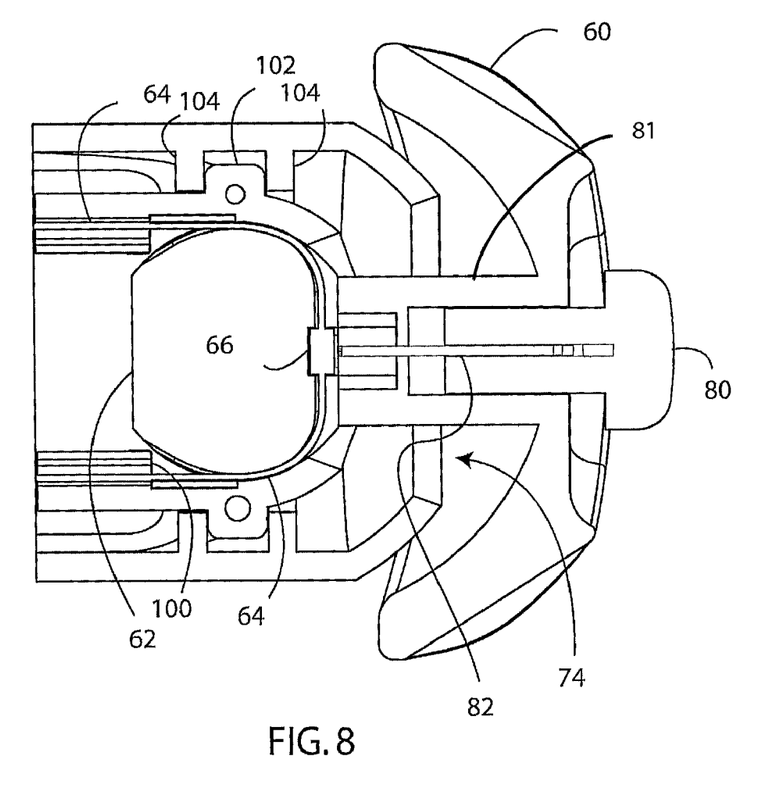
FIG. 8 is a top cross-section view of the proximal end of the handle of the surgical instrument of FIG. 1.

Referring also to FIGS. 4 and 8, a cable 64 extends through the lumen of the shaft 4 proximally into the housing 20 of the handle 2. The cable 64 wraps around an rotary articulator 62 and then extends distally back out of the housing 20 into the lumen of the shaft 4. The rotary articulator 62 may be spherical, partially spherical, spheroidal, cylindrical, or may have any other suitable shape. The cable 64 may be fixed to the rotary articulator 62, such as by a cylinder 66, tab, or other wider structure that is fixed to the cable 64. The cylinder 66 is held by a corresponding detent in the rotary articulator 62, such as in its proximal end. The cylinder 66 may be fixed to the rotary articulator 62, such as by welding, adhesive, crimping, pressure fitting, or any other or additional structure, mechanism or method. Alternately, the cable 64 may be fixed directly to the rotary articulator 62, such as by welding, adhesive, crimping, pressure fitting, or any other or additional structure, mechanism or method. The cable 64 may be wrapped around the rotary articulator 62 once, or more than once. Advantageously, the cable 64 is wrapped around the proximal end of the rotary articulator 62 such that the cable 64 is routed proximally from the shaft 4 along one side of the rotary articulator 62, around the proximal end of the rotary articulator 62, then distally along the other side of the rotary articulator 62 to the shaft 4. Referring also to FIG. 6, the cable 64 is routed through the handle 2 such that it is capable of moving substantially freely. The clamp controller 32 may include two or more ramps 112 or apertures that receive the cable 64 and allow the cable 64 to smoothly enter the lumen of the shaft 4. The clamp controller 32 may also include a tunnel 114 or opening extending longitudinally therethrough to allow the actuation cable 110 to extend therethrough into the lumen of the shaft 4.

Figure 10:
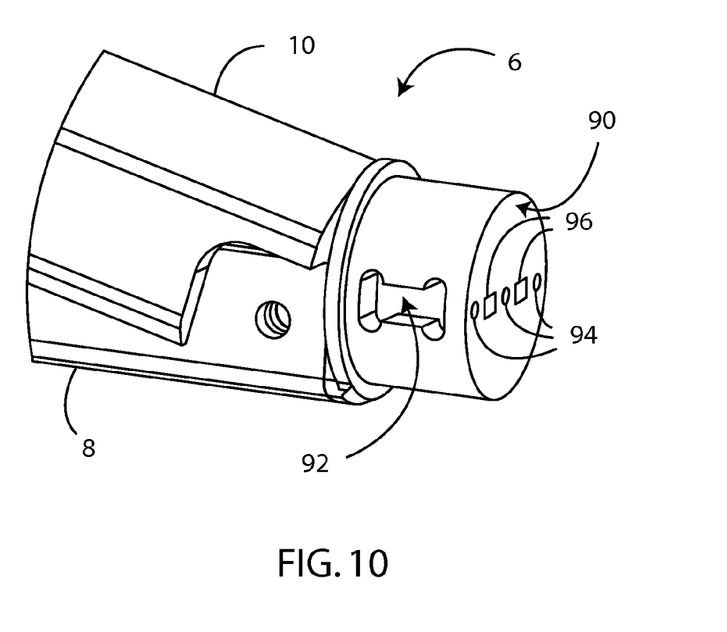
FIG. 10 is a perspective view of an exemplary end effector of the surgical instrument of FIG. 1.

Referring also to FIG. 10, the proximal end of the end effector 6 may include a bulkhead 90 in which one or more apertures 94 are defined. Advantageously, both ends of the cable 64 extend through separate apertures 94, where those apertures 94 are laterally spaced apart from one another. Advantageously, those two apertures 94 through which the cable 64 extends and the longitudinal centerline of the shaft 4 are aligned along a straight line. Distal to the bulkhead 90, the ends of the cable 64 may be knotted, fixed to structures wider than the diameter of the aperture 94, or otherwise secured distal to the bulkhead 90. The cable 64 may be under tension when the ends of the cable 64 are secured relative to the bulkhead 90. Alternately, one or more of the apertures 94 may be omitted, and at least one end of the cable 64 is fixed directly to the bulkhead, such as by welding, adhesive, crimping, pressure fitting, or any other or additional structure, mechanism or method. Alternately, the bulkhead 90 may be fixed to the shaft 4, rather than the end effector 6. Alternately, the bulkhead 90 may be any rigid structure substantially fixed relative to the distal end of the shaft 4.

Figure 9:
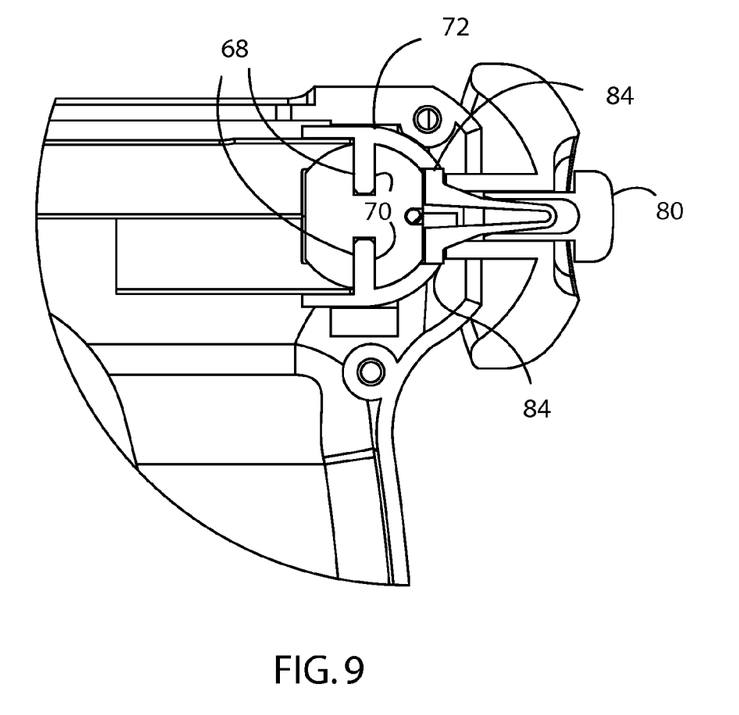
FIG. 9 is a side cutaway view of the proximal end of the handle of the surgical instrument of FIG. 1.

The rotary articulator 62 may be held in a cradle 72 within the housing of the handle 2. The cradle 72 holds the rotary articulator 62 in a substantially fixed longitudinal position within the handle 2. The proximal end of the cradle 72 may be shaped substantially the same as the proximal surface of the rotary articulator 62, such that the rotary articulator 62 can rotate smoothly in the cradle 72. One or more pins 100, lips or tabs may extend inward from the distal end of the cradle 72 to retain the rotary articulator 62 within the cradle 72 while still allowing the rotary articulator 62 to rotate. Alternately, the cradle 72 is not used, and the housing 20 or other component of the handle 2 holds the rotary articulator 62 in a substantially fixed longitudinal position within the handle 2. Referring also to FIG. 9, at least one axle 68 may extend from the cradle 72 into a corresponding slot 70 defined in the rotary articulator 62. The axle or axles 68 define an axis about which the rotary articulator 62 is rotatable. Alternately, the axles 68 are not utilized, and the rotary articulator 62 is otherwise constrained to rotate about one or more axes.

Referring also to FIG. 9, an articulation control 60 may be connected to the rotary articulator 62, and extend through an opening 74 in the housing 20 as well as an opening 88 in the proximal end of the cradle 72. The articulation control 60 may be fixed to the rotary articulator 62, and may be connected to it in any suitable manner, such as by fasteners, adhesive, welding, or any other suitable structure, mechanism or method. The articulation control 60 is configured such that motion of the articulation control 60 from side to side causes rotation of the rotary articulator 62 about an axis, such as defined by one or more of the axles 68. A tube 81 may extend from the articulation control 60 toward the rotary articulator, and a pin 80 may be positioned partially in the lumen of and extending proximally from that tube 81. The pin 80 may be slidable within the lumen of the tube 81. A clip 82 is fixed to the pin 80, and extends distally into the tube 81. The clip 82 may includes two legs 84 biased outward relative to the longitudinal centerline of the tube 81. The legs 84 may be generally symmetrical and generally thin and planar, or may be otherwise configured. The legs 84 may be spaced apart from one another.

The opening 88 in the proximal end of the cradle 72 may have a plurality of teeth 86 defined along its upper and/or lower edges. The clip 82 is configured to slide between adjacent teeth 86 when the pin 80 moves distally. The pin 80 may be biased distally, or may be configured to remain placed where the user sets it. When the pin 80 is moved proximally, the legs 84 are positioned proximal to the proximal edges of the teeth 86, such that the articulation control 60 may be rotated left or right in order to rotate the rotary articulator 62. The clip 82 optionally may be shaped such that when the pin 80 is moved proximally, the outer edges of the legs 84 encounter the distal end of the tube 81 and are collected down by that contact. Such motion may facilitate free motion of the rotary articulator 62. When the pin 80 is moved distally, it enters a space between two teeth 86, thereby preventing rotation of the rotary articulator 62 and fixing the rotary articulator 62 in place. The teeth 86 may be angled such that if a leg 84 encounter a space between teeth 86 while moving distally, the leg 84 is directed to the left or right into the space between adjacent teeth 86. The spacing between the teeth 86 defines the number of discrete positions at which the rotary articulator 62 can be selectively fixed. Alternately, the teeth 86 may be omitted, and any other suitable mechanism may be used to selectively fix the rotary articulator 62, either in one of a number of discrete positions, or along an infinitely variable continuum.

As the rotary articulator 62 is rotated about the axle or axles 68, the cable 64 transmits that rotation to the end effector 6, as described in greater detail below. The rotary articulator 62 may provide for articulation about one axis. Optionally, a rototube 50 may provide for rotation about a second axis. Alternately, the rotary articulator 62 is not used, and the rototube 50 provides rotation about its axis. Where the rototube 50 is utilized, the cradle 72 may be fixed to the proximal end of the rototube 50. The cradle 72 may include one or more lateral protrusions 102 that is held between two ridges 104 defined in the inner surface of the housing 20 of the handle 2. The ridges 104 may be generally parallel to one another, and each in a plane generally perpendicular to the longitudinal centerline of the rototube 50. In this way, the cradle 72 is able to rotate about the longitudinal axis of the rototube 50, along with a remainder of the rototube 50, while remaining at substantially the same longitudinal position relative to the handle 2. Referring also to FIG. 6, the distal end of the rototube necks down to connect to the proximal end of the shaft 4. The shaft 4 is configured to be held by the handle 2 in such a manner that the shaft 4 is rotatable relative to the handle. The aperture 106 at the distal end of the handle 2 supports the shaft 4, but is not fixed to the shaft 4, such that the shaft 4 is rotatable within the aperture 106. By rotating the rototube 50 about its longitudinal axis, another axis of rotation is provided for the end effector 6 in addition to the axis of rotation provided by the rotary articulator 62. The rototube 50 may be actuated to rotate about its longitudinal axis in any suitable manner. As one example, after the rotary articulator 62 is locked in place as described above, the articulation control 60 may be rotated about its axis, thereby rotating the rototube 50 about its longitudinal axis as well. As another example, the articulation control 60 may be actuated to rotate the rototube 50 prior to locking the rotary articulator 62 in place. As another example, the articulation control 60 may be free to both rotate the rototube 50 and the rotary articulator 62 at the same time.

Figure 5:
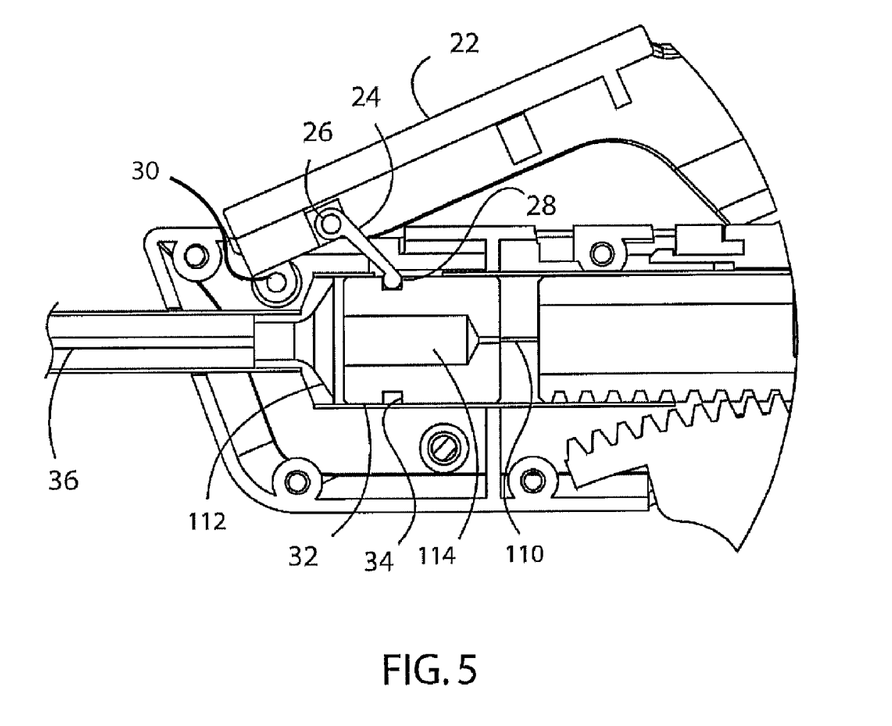
FIG. 5 is a detail side cutaway view of the distal end of the handle of the surgical instrument of FIG. 1.

Referring to FIGS. 4-5, the handle 2 may include a clamping trigger 22 for actuating the end effector 6 to move to a clamped position or state, and an actuating trigger 40 for actuating the end effector 6 to deploy staples and/or otherwise actuate the end effector 6. Where the end effector 6 is not configured to clamp tissue, the clamping trigger 22 may be omitted. The clamping trigger 22 may be configured in any suitable manner that allows it to actuate the end effector 6 to a clamped position or state. As one example, an aperture may be defined through the housing 20 such that the distal end of the clamping trigger 22 enters the housing 20. A clamping axle 30 may be defined in the housing 20 and extend inward from the inner surface of the housing 20, and the clamping trigger 22 may be configured to rotate about that clamping axle 30. The clamping trigger 22 may have a pivot 26 defined therein, where that pivot 26 is oriented substantially perpendicular to the longitudinal centerline of the proximal end of the shaft 4. A linkage 24 is rotatably connected to the pivot 26 at or near one end, and the other end of the linkage 24 is positioned in a notch 34 in a clamp controller 32. The clamp controller 32 may be generally cylindrical, and the notch 34 defined therein may extend around part or all of the circumference of the clamp controller 32. The notch 34 may be oriented substantially perpendicular to the longitudinal centerline of the proximal end of the shaft 4. As the free end of the clamping trigger 22 is depressed, and the clamping trigger 22 rotates about the clamping axle 30, the proximal end 28 of the linkage 24 moves proximally, urging the clamp controller 32 proximally to actuate the end effector 6 to clamp, as described in greater detail below.

The actuating trigger 40 may be configured in any suitable manner that allows it to actuate the end effector 6 to deploy staples and/or otherwise actuate the end effector 6. A trigger axle 42 may be defined in the housing 20 and extend inward from the inner surface of the housing 20, and the actuating trigger 40 may be configured to rotate about that trigger axle 42. The trigger 40 is advantageously oriented to be compressed by hand by the user. The upper surface of the trigger 40 may include one or more teeth 44 defined therein. Alternately, the teeth 44 may be defined in a different part of the trigger 40. Correspondingly, one or more teeth 48 may be defined in the lower surface of an actuation controller 46, and configured to engage the teeth 44 of the trigger 40. As the trigger 40 is depressed, the trigger 40 rotates about the trigger axle 42, such that the upper surface of the trigger 40 moves proximally. As that upper surface moves proximally, the teeth 44 of the trigger 40 engage the teeth 48 of the actuation controller 46 and urge the actuation controller proximally to actuate the end effector 6, as described in greater detail below. The rototube 50 may include at least one cutout 52 defined therein to allow the rototube 50 to rotate about its longitudinal axis without colliding with the upper end of the trigger 40.

Figure 11:
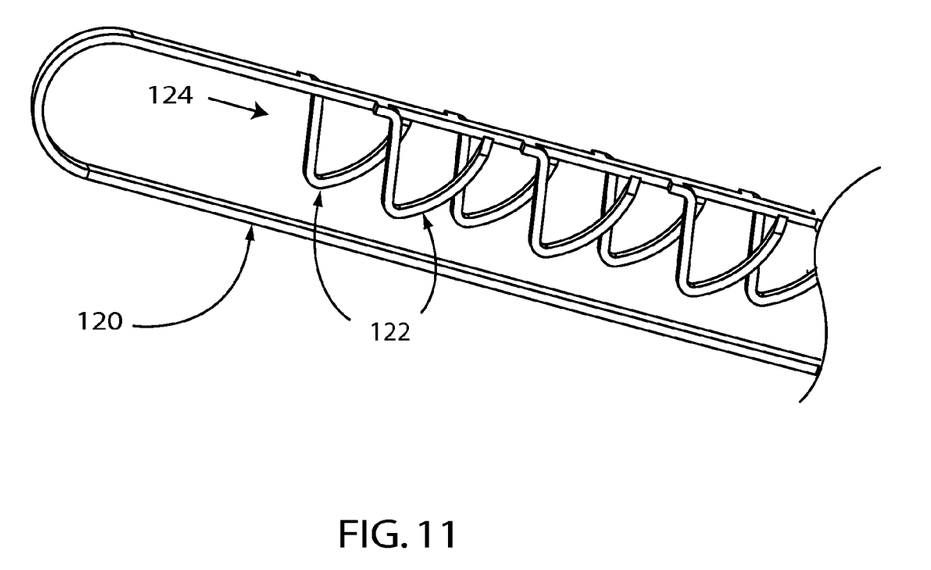
FIG. 11 is a perspective view of an exemplary feeder belt with two rows of staples frangibly connected thereto.

A portion of at least one feeder belt may extend from the shaft 4 into, or be positioned within, the end effector 6. Where at least one feeder belt extends from the shaft 4 through the bulkhead 90 into the end effector 6, each feeder belt may extend through the feeder belt access apertures 96 in the bulkhead 90. The feeder belt 120 and its associated hardware may be as set forth in the Endocutter Applications and in FIG. 11. In the interest of brevity, the feeder belt 120 will not be described in detail herein. Each feeder belt 120 may be a long, narrow, thin strip of material from which one or more staples 122 extend. At least one staple 122 may be frangibly connected to the feeder belt 120 at one end, with the other end of the staple being free. One row 124 of staples 122 may be located along each side of the feeder belt 120. Each feeder belt 120 may be movable relative to the end effector 6, as set forth in the Endocutter Applications, such that the end effector 6 can be actuated multiple times without the need to exchange cartridges or remove the end effector 6 from the patient between actuations. The end effector 6 may be configured generally as set forth in the Endocutter Applications, as one example, or may be configured differently.

The end effector 6 optionally may include at least one engagement feature 92 defined therein, or thereon. The engagement feature 92 connects to a corresponding feature on the shaft 4, such that the end effector 6 can be removed from the shaft 4, and a new end effector 6 connected to the shaft 4. That is, the end effector 6 optionally may be interchangeable on the shaft 4. In this way, the end effector 6 can be removed for sterilization of a remainder of the surgical instrument 1, and/or the end effector 6 can be reloaded during a surgical procedure with a fresh end effector 6 of the same type, or a different end effector 6 of a different type. If so, the feeder belt optionally may not extend through the bulkhead 90, such that the apertures 96 need not be provided in the bulkhead 90.

Operation

The end effector 6 of the surgical instrument 1 is introduced into the body of the patient, whether through a trocar port, a small incision for minimally invasive surgery, or a larger incision for conventional open surgery. At least part of the shaft 4 may follow the end effector 6 into the patient. The end effector 6 is positioned by the user at a surgical site. As one example, where the end effector 6 is an endocutter such as described in the Endocutter Applications, a surgical site is located on a blood vessel which is to be transected. For clarity, this document describes the exemplary operation of the surgical instrument 1 for transection of a blood vessel. However, the use of the surgical instrument 1 is not limited to blood vessel transection; the surgical instrument 1 may be used to perform any other suitable procedure at any other surgical site in the body. For example, the surgical instrument 1 may be used to transect a bile duct, to remove a diseased appendix, to transect gastrointestinal tissue, and/or to transect soft tissue or organs. Alternately, the end effector 6 may be used to treat a surface of the body, such that the end effector 6 is not inserted into the patient.

The end effector 6 may be inserted into the body of a patient through an opening, incision, trocar port or other aperture, in the open or closed position. The end effector 6 is then advanced to a site where tissue to be treated is located. An endoscope, inserted through the same or a different opening, incision, trocar port, or aperture may be used to guide the end effector 6 into position, where the end effector 6 is utilized for a minimally-invasive surgical procedure. Alternately, a camera (not shown) is attached to the end effector 6 and/or shaft 4 of the surgical instrument 1; a light source and any other necessary auxiliary hardware may be attached to the end effector 6 and/or shaft 4 as well. If so, the surgeon may visualize the surgical site solely utilizing the surgical instrument 1, thereby reducing the number of openings that are made in the patient and rendering the surgical procedure more minimally invasive.

The surgeon advances the end effector 6 into proximity to the surgical site. The end effector 6 fortuitously may be properly oriented relative to the surgical site at this time. If so, the end effector 6 need not be articulated. If the end effector 6 is not properly oriented relative to the surgical site, then the end effector 6 may be articulated. The surgeon first may move the articulation control 60, such as with his or her thumb. The pin 80 is moved proximally, if it is not already in that position whether due to its affirmative motion proximally by the surgeon, or due to a force biasing the pin 80 proximally. As a result, the articulation control 60, and consequently the rotary articulator 62, is free to rotate left and right about the axle or axles 68. The cable 64 is under tension, and is fixed to the rotary articulator 62 as described above. As the surgeon rotates the articulation control 60 to the left, for example, the cable 64 exerts a force in the proximal direction on the right side of the bulkhead 90 of the end effector 6, at a point lateral to and spaced apart from the longitudinal centerline of the end effector 6, such as at an aperture 94 on the right side of the bulkhead 90. As a result, this force exerts a torque about the yaw axis, causing the shaft 4 to bend to the right due to bending in the articulated region 12. As the only flexible region between the bulkhead 90 of the end effector 6 and the handle 2, bending is focused in and substantially restricted to the articulated region 12. Because the articulated region 12 is flexible, and because springs or other force transmission members are advantageously not used in articulating the shaft 4 and/or returning the shaft 4 to a neutral position, the surgeon need not overcome a substantial force in order to articulate the end effector 6, and can move the articulation control 60 one-handed. The surgeon moves the articulation control 60 left or right until the desired orientation is reached, and then moves the pin 80 distally. The surgeon may release the pin 80, if it is biased distally, or may affirmatively move the pin 80 distally. As the pin 80 moves distally, the legs 84 of the clip 82 move distally, and may move apart from one another as well. Each leg 84 enters a space between adjacent teeth 86 defined in the opening 88, or between a tooth 86 and a wall defining the leftmost or rightmost edge of the opening 88. As the legs 84 enter those spaces, the orientation of the end effector 6 may change slightly; the spaces between teeth 86 define discrete positions, and the teeth 86 are tapered to a point extending in the proximal direction to assist the legs 84 in sliding therebetween and slightly reorienting the end effector 6 as a result. The rotary articulator 62 is thus locked in place. If the surgeon is unhappy with the resulting orientation, or changes his or her mind, the pin 80 may be retracted proximally, and the articulation control 60 may be moved again. The rotary articulator 60 is then locked in place in the desired position, as set forth above.

Next, if necessary, the surgeon may rotate the rototube 50 to orient the end effector 6 more precisely. To do so, the surgeon may rotate the articulation control 60 about its longitudinal axis. With the rotary articulator 62 locked in place relative to the cradle 72, and with the cradle 72 being fixed to the rototube 50, the rotation of the articulation control 60 about its longitudinal axis causes rotation of the rototube 50. Alternately, the rototube 50 may be actuated by a separate control. As the rototube 50 rotates, the shaft 4 (the proximal end of which is at least rotationally fixed to the distal end of the rototube 50) rotates as well, about the longitudinal axis of the part of the shaft 4 located proximal to the articulated section 12 of the shaft 4. The articulation control 60 may then be locked into position in any suitable manner, to prevent further movement of the end effector 6. Alternately, the articulation control 60 need not be locked further; for example, clamping of the end effector 6 onto tissue at or in proximity to the surgical site may provide sufficient restriction of further motion of the end effector 6.

In this way, the end effector 6 is articulable in two degrees of freedom, about the roll and yaw axes. Although articulation of the end effector 6 has been described in a particular order, the surgeon could reverse the order, such that the rototube 50 is rotated first, then the articulation left or right about the yaw axis is performed. To do so, the surgeon may simply lock the rotary articulator 62 in a random position, rotate the rototube 50, then unlock the rototube 50 and articulate the end effector 6 to cause bending of the shaft 4 in the articulated region 12. Alternately, the surgeon may articulate the end effector 6 about both axes at the same time, if desired, then lock the rotary articulator 62 in place.

The end effector 6 is now ready for actuation. The end effector 6 is in the open position as it is moved into position at the surgical site. The end effector 6 may be located in the desired position relative to the surgical site at the end of the articulation process. Alternately, the shaft 4 may be advanced or moved after articulation to place the properly-oriented end effector 6 at the surgical site. Where the end effector 6 is used to perform transection of a blood vessel, the end effector 6 is in the open configuration, and placed over the blood vessel to be transected until the blood vessel is located between the staple holder 8 and the anvil 10 of the end effector 6. The end effector 6 is then moved to the closed position. To do so, the clamping trigger 22 may be actuated. As the clamping trigger 22 is moved toward the housing 20 of the handle 2, the pivot 26 of the trigger 22 moves toward the housing 20 as well, causing the linkage 24 to rotate about the pivot 26 and move toward the housing, and causing the proximal end of the linkage 24 to move proximally. As set forth above, the proximal end of the linkage 24 resides at least partially within the notch 34 in the clamp controller 32, and the proximal motion of the proximal end of the linkage 24 urges the clamp controller 32 proximally. The clamp controller 32 may be connected to a clamp cable 36, such that proximal motion of the clamp controller 32 pulls the clamp cable 36 proximally. The clamp cable 36 may extend into the end effector 6 through an aperture 94 in the bulkhead 90 of the end effector 6. Proximal motion of the clamp cable 36, and/or tensioning of the clamp cable 36, may move the end effector 6 from the open position to the closed position, such as set forth in the Endocutter Applications.

The end effector 6 then may be actuated. The surgeon may squeeze the actuating trigger 40, which rotates about the trigger axle 42. As the trigger 40 rotates, the teeth 44 of the trigger 40 engages the teeth 48 of the actuation controller 46. Thus, as the upper surface of the trigger 40 moves proximally, the teeth 44 urge the teeth 48, and thereby the actuation control 46, proximally. The actuation controller 46 may be connected to an actuation cable 110, such that proximal motion of the actuation controller 46 pulls the actuation cable 110 proximally. The actuation cable 110 may extend into the end effector 6 through an aperture 94 in the bulkhead 90 of the end effector 6. Proximal motion of the actuation cable 110, and/or tensioning of the clamp cable 36, may actuate the end effector 6 such as set forth in the Endocutter Applications. For example, the staple holder 8 may deploy staples into the blood vessel and against the anvil 10, along two or more lines, and a knife may cut the blood vessel between two such lines.

As the actuation controller 46 moves proximally, the slider 54 connected to the actuation controller 46 moves proximally as well. The slider 54 extends out of the housing 20, such as through a slot 61 in the upper surface of the housing 20, and provides a visual indication that the end effector 6 has been actuated. The actuation of the end effector 6 is thus complete. The clamping trigger 22 may be moved away from the housing 20, thereby releasing tension on the clamp cable 36, allowing the end effector 6 to move back to the open position. Advantageously, the end effector 6 is biased to the open position, such as by a spring. If the surgical procedure is complete, the end effector 6 may be withdrawn from the patient.

If the surgeon desires to use the end effector 6 at a different location within the patient, and the surgical instrument 1 includes one or more feeder belts, as described in the Endocutter Applications, the feeder belt or belts may be advanced, placing a fresh set of staples in position for deployment within the staple holder. Such advancement may be accomplished as set forth in the Endocutter Applications. Optionally, the slider 54 may be used to reset the surgical instrument 1 and advance the feeder belt or belts. For example, the slider may engage the driver and move the driver distally, thereby causing the ratchet pawl fixed to the driver to engage a corresponding face of the top plate of the feeder belt and advance the top plate distally, as set forth in the Endocutter Applications. In this way, the slider 54 also acts to indicate that the surgical instrument 1 has been reset and is ready to be fired again. The end effector 6 need not be withdrawn from the body of the patient during advancement of the feeder belts. The feeder belts may extend through the lumen of the shaft 4 into the housing 20 of the handle 2. If so, the feeder belts may enter the end effector 6 through the feeder belt access apertures 96 in the bulkhead 90 of the end effector 6. The surgeon may release the end effector 6 from its selected, articulated position, such as by moving the pin 80 proximally out of engagement with the teeth 86. The surgeon may then articulate the end effector 6 differently for use at a different surgical site, as set forth above.

While the invention has been described in detail, it will be apparent to one skilled in the art that various changes and modifications can be made and equivalents employed, without departing from the present invention. It is to be understood that the invention is not limited to the details of construction, the arrangements of components, and/or the method set forth in the above description or illustrated in the drawings. Statements in the abstract of this document, and any summary statements in this document, are merely exemplary; they are not, and cannot be interpreted as, limiting the scope of the claims. Further, the figures are merely exemplary and not limiting. Topical headings and subheadings are for the convenience of the reader only. They should not and cannot be construed to have any substantive significance, meaning or interpretation, and should not and cannot be deemed to indicate that all of the information relating to any particular topic is to be found under or limited to any particular heading or subheading. Therefore, the invention is not to be restricted or limited except in accordance with the following claims and their legal equivalents.

What is claimed is:

1. Surgical apparatus, comprising:
   an end effector wherein said end effector includes at least one opening in the proximal end thereof;
   a shaft connected to said end effector, wherein said shaft comprises a surface, a lumen defined therein, an outer perimeter about the longitudinal centerline, and an articulated region including a plurality of slots defined in said shaft, wherein at least two said slots extend over greater than half of the perimeter of said shaft and are oriented relative to one another such that every line on the surface of said shaft that is parallel to the longitudinal centerline of said shaft crosses at least one said slot; and
   at least one feeder belt including a plurality of staples, wherein each said staple comprises a first end frangibly affixed to a corresponding said feeder belt, wherein each said first end is affixed to said feeder belt at a location laterally spaced from the longitudinal centerline of said feeder belt, and a second free end; and wherein said staples form at least one row, each said row including at least two said staples, wherein at least one said feeder belt extends along said lumen of said shaft and into said end effector through said opening in said proximal end of said end effector.

2. The surgical apparatus of claim 1, wherein at least one said slot is angled.

3. The surgical apparatus of claim 1, further comprising at least one cable extending from said end effector through said lumen.

4. The surgical apparatus of claim 1, wherein said end effector is interchangeable on said shaft.

5. The surgical apparatus of claim 1, wherein a proximal portion of said shaft is rotatable about its longitudinal axis.

6. The surgical apparatus of claim 1, wherein said shaft is generally tubular.

* * * * *